United States Patent
Li et al.

(10) Patent No.: US 12,151,070 B2
(45) Date of Patent: Nov. 26, 2024

(54) DRUG ELUTING BALLOON AND BALLOON CATHETER

(71) Applicant: SHANGHAI MICROPORT MEDICAL (GROUP) CO., LTD., Shanghai (CN)

(72) Inventors: Meng Li, Shanghai (CN); Lu Chen, Shanghai (CN); Junfei Li, Shanghai (CN)

(73) Assignee: SHANGHAI MICROPORT MEDICAL (GROUP) CO., LTD, Shanghai (CN)

( * ) Notice: Subject to any disclaimer, the term of this patent is extended or adjusted under 35 U.S.C. 154(b) by 842 days.

(21) Appl. No.: 17/296,446

(22) PCT Filed: Oct. 31, 2019

(86) PCT No.: PCT/CN2019/114714
§ 371 (c)(1),
(2) Date: May 24, 2021

(87) PCT Pub. No.: WO2020/103667
PCT Pub. Date: May 28, 2020

(65) Prior Publication Data
US 2022/0016398 A1    Jan. 20, 2022

(30) Foreign Application Priority Data

Nov. 23, 2018  (CN) .......................... 201811423293.9

(51) Int. Cl.
*A61M 25/10* (2013.01)
*A61L 29/08* (2006.01)
(Continued)

(52) U.S. Cl.
CPC ........... *A61M 25/10* (2013.01); *A61L 29/085* (2013.01); *A61L 29/141* (2013.01);
(Continued)

(58) Field of Classification Search
CPC .......... A61M 2025/1075; A61M 25/10; A61M 25/0045; A61M 2025/105;
(Continued)

(56) References Cited

U.S. PATENT DOCUMENTS

| 4,426,432 A * | 1/1984 | Sawada | G03G 5/0688 430/72 |
|---|---|---|---|
| 6,387,410 B1 * | 5/2002 | Woolfe | A61K 9/209 424/490 |

(Continued)

FOREIGN PATENT DOCUMENTS

| CN | 103990221 A | 8/2014 |
|---|---|---|
| CN | 204050424 U | 12/2014 |

(Continued)

*Primary Examiner* — Michael J Tsai
*Assistant Examiner* — Rachel T. Smith
(74) *Attorney, Agent, or Firm* — MUNCY, GEISSLER, OLDS & LOWE, P.C.

(57) ABSTRACT

Disclosed is a drug eluting balloon for a balloon catheter. The drug eluting balloon comprises a balloon body (100) and a coating (200), and the coating (200) comprises a water-soluble adhesive layer (210), an isolating layer (220) and a drug layer (230) from the inside out. After the drug eluting balloon is pushed to a diseased part, the balloon body (100) is expanded, and the water-soluble adhesive layer (210) dissolves due to scouring by a blood flow, such that the isolating layer (220) and the drug layer (230) are separated from an outer surface of the balloon body (100) and adhere to a blood vessel wall. The provision of the isolating layer (220) can effectively suppress the water-soluble adhesive layer (210) from removing part of the drug layer (230) during dissolution, and after the drug layer (230) adheres to and makes contact with the blood vessel wall, the isolating layer can also reduce the scouring effect on the drug layer (230) by the blood flow, thereby reducing the loss of drugs, allowing the drugs to be taken in by the blood vessel wall to (Continued)

the greatest extent, greatly improving the utilization rate of the drugs and improving the treatment effect while also preventing toxic and side effects brought about by large doses of the drugs. Moreover, the isolating layer (220) can also realize the slow release of the drug layer (230), such that the drug layer (230) can provide treatment for a long time, and a good treatment effect can be obtained.

13 Claims, 1 Drawing Sheet

(51) Int. Cl.
    *A61L 29/14*     (2006.01)
    *A61M 25/00*     (2006.01)

(52) U.S. Cl.
    CPC ... *A61M 25/0045* (2013.01); *A61M 2025/105* (2013.01); *A61M 2025/1075* (2013.01)

(58) Field of Classification Search
    CPC .. A61M 2025/1031; A61M 2025/1081; A61M 2025/1086; A61M 25/1029; A61M 25/1027; A61M 25/104; A61M 25/1002; A61L 29/085; A61L 29/141; A61L 2300/416; A61L 2300/608; A61L 2420/08; A61L 29/16; A61L 29/08; A61L 29/14; A61L 2300/606; A61L 2300/412; A61L 2300/428; A61L 2420/02; A61L 2420/06; A61F 2/958; A61F 2250/0067

See application file for complete search history.

(56) References Cited

U.S. PATENT DOCUMENTS

| | | |
|---|---|---|
| 2011/0054396 A1 | 3/2011 | Kangas et al. |
| 2011/0071499 A1* | 3/2011 | Hakimimehr ........ A61K 9/7084 |
| | | 604/509 |
| 2012/0078227 A1 | 3/2012 | Kangas |
| 2012/0095396 A1 | 4/2012 | Radhakrishnan et al. |
| 2013/0018448 A1 | 1/2013 | Folon et al. |
| 2015/0231362 A1 | 8/2015 | Orlowski |

FOREIGN PATENT DOCUMENTS

| | | | |
|---|---|---|---|
| CN | 104874090 A | 9/2015 | |
| CN | 104936629 A | 9/2015 | |
| WO | WO-2014127718 A1 * | 8/2014 | ........... A61L 29/085 |
| WO | WO-2014143061 A1 * | 9/2014 | ........... A61L 29/085 |
| WO | WO2015070814 A1 | 5/2015 | |

\* cited by examiner

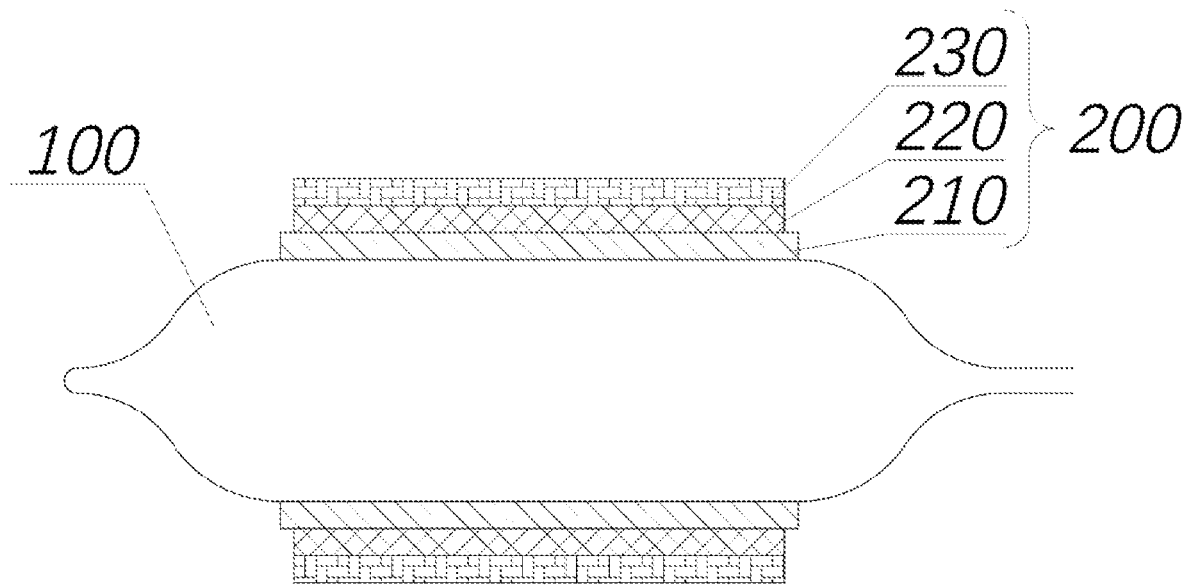

DRUG ELUTING BALLOON AND BALLOON CATHETER

TECHNICAL FIELD

The present application relates to the field of medical instruments and, in particular, to a drug eluting balloon and a balloon catheter.

BACKGROUND

Cardiovascular disease is a significant threat to human health. Percutaneous coronary intervention (PCI) has a variety of advantages including small trauma and reduced incidence of vascular restenosis and has gradually become the first choice for the treatment of obstructive coronary heart disease. The current mainstream therapeutic regimen is the drug eluting stents (DESs), which are originally developed to address the high incidence of in-stent restenosis following the implantation of bare metal stents (BMSs). DESs are loaded with an anti-proliferative drug, which can significantly inhibit intimal hyperplasia of a blood vessel and thus lower the likelihood of in-stent restenosis. However, drug eluting stents are also challenged with a number of problems such as the anaphasis in-stent thrombosis and increased blood vessel healing time. As the number of patients who receive PCI increases every year, ISR has become a problem that requires to be tackled urgently.

The recent drug eluting balloon (DEB) that combines the traditional balloon angioplasty with the latest drug release technique has attracted increasing attention due to the advantages including intervention without implantation, no risk of thrombosis and a rapid therapeutic effect. Functioning like a DES, a drug eluting balloon can deliver an anti-proliferative drug coated on the surface of the balloon uniformly to the blood vessel wall of a lesion, thus inhibiting intimal hyperplasia and reducing the likelihood of in-stent restenosis.

However, the design of a drug eluting balloon has to trade off adhesion performance of the drug to the balloon surface against detachment of the drug from the balloon surface during implantation. A drug eluting balloon usually maintains a dilated configuration for a very short time, e.g., about only 30-60 s, during its use in therapeutic treatment, causing a very short time period for the drug thereon to keep contact with the blood vessel wall. In such a short time period, complete detachment of the drug is difficult to achieve. Coupled with impact of blood flow, ultimately, it may be the case that only a limited fraction of the drug can be taken up by the blood vessel, leading to a poor inhibitory effect on intimal hyperplasia. On the other hand, although increasing the drug load on the balloon may raise the drug's intake, this may induce certain toxic side effects due to overdosing.

SUMMARY

An object of the present application is to provide a drug eluting balloon and a balloon catheter, in which the design of an isolating layer separating a water-soluble adhesive layer from a drug layer allows facilitating detachment of the drug from the balloon surface at a lesion site and further suppressing flush action of blood flow on the drug. In this way, maximum intake of the drug by the wall of the blood vessel is able to be achieved, thereby improving utilization of the drug and allowing an optimized therapeutic effect as well as avoiding toxic side effects of the drug.

To solve the above problem, present application provides a drug eluting balloon comprising a balloon body and a coating layer arranged on an outer surface of the balloon body. The coating layer comprises a water-soluble adhesive layer, an isolating layer and a drug layer that are arranged sequentially in this order from inside outward. The water-soluble adhesive layer all or partial of the outer surface of the balloon body, and the isolating layer completely or incompletely covers the water-soluble adhesive layer.

Optionally, the isolating layer comprises a water-resistant degradable material selected from the group consisting of cellulose-based materials, polyester-based materials, chitosan-based materials, polyamino acid, chitins, polyvinyl acetals and combinations thereof.

Optionally, the isolating layer further comprises a plasticizer selected from the group consisting of glycerol, castor oil, olive oil and combinations thereof.

Optionally, the isolating layer may be present in the coating layer at a weight percentage ranging from 1% to 20%, preferably from 5% to 10%. A weight ratio of the water-resistant degradable material to the plasticizer ranges from 1:1 to 1:2. Optionally, the weight ratio of the water-resistant degradable material to the plasticizer ranges from 1:1.2 to 1:1.5.

Optionally, at least one end portion of the water-soluble adhesive layer is not covered by the isolating layer.

Optionally, the water-soluble adhesive layer covers the outer surface of the balloon body in a grid, stripe or spiral pattern.

Optionally, the water-soluble adhesive layer comprises a water-soluble macromolecular material selected from the group consisting of starch-based natural macromolecular materials, synthetic water-soluble macromolecular materials and combinations thereof.

Optionally, the water-soluble adhesive layer is present in the coating layer at a weight percentage ranging from 15% to 50%, preferably from 30% to 40%. The water-soluble macromolecular material comprises a starch-based natural macromolecular and a synthetic water-soluble macromolecular material, and the weight ratio of starch-based natural macromolecular material to synthetic water-soluble macromolecular material ranges from 1:1 to 5:1. Optionally, the weight ratio of the starch-based natural macromolecular to the synthetic water-soluble macromolecular material ranges from 2:1 to 4:1.

Optionally, the drug layer may comprise a drug and a macromolecular excipient, wherein the macromolecular excipient is selected from the group consisting of partially hydrolyzed polyvinyl alcohols, polyvinylpyrrolidone and combinations thereof.

Optionally, the drug layer is present in the coating layer at a weight percentage ranging from 30% to 80%. Optionally, the drug layer is present in the coating layer at a weight percentage ranging from 50% to 75%.

Optionally, a weight ratio of the drug to the macromolecular excipient ranges from 1:1 to 1:5. Optionally, the weight ratio of the drug to the macromolecular excipient ranges from 1:2 to 1:3.

To solve the above problem, present application also provides a balloon catheter comprising the drug eluting balloon as defined above.

In the drug eluting balloon and balloon catheter provided in present application, the coating layer is arranged on the outer surface of the balloon body and comprises the water-soluble adhesive layer, the isolating layer and the drug layer that are stacked from inside outward sequentially in this order. In this way, when the drug-eluting balloon is delivered to a lesion site, the balloon body is dilated and the water-soluble adhesive layer then dissolves under the flush action of blood flow, thereby allowing the isolating layer and the drug layer to be divorced from the outer surface of the balloon body and to adhere to the blood vessel wall. Moreover, the isolating layer is able to effectively reduce loss of the drug layer taken away by the dissolution of the water-soluble adhesive layer and further allows suppressing the flush action of blood flow on the drug layer after the adherence and contact of the drug layer with the blood vessel wall to reduce drug loss. In this way, maximum intake of the drug by the blood vessel the wall is able to be achieved, thereby significantly improving utilization of the drug and allowing an optimized therapeutic effect without an increased dosage of the drug, as well as avoiding any toxic side effect incurred by the overdosing of the drug. In addition, the isolating layer further allows significantly avoiding the flush action of blood flow on the drug layer, so that sustained release of the drug from the drug layer is able to be achieved to get a prolonged period of therapeutic action, thereby further optimizing the therapeutic effect. Notably, when cross-linked, the macromolecular excipient in the drug layer exhibits a reduced water solubility and provides a network in which the drug is stored. As a result, elution of the drug during delivery of the balloon is able to be reduced effectively.

BRIEF DESCRIPTION OF THE DRAWINGS

As will be appreciated by those of ordinary skill in the art, the following accompanying drawing is provided to facilitate understanding of the present application and is not intended to limit the scope thereof in any sense.

The sole FIGURE is a schematic diagram showing a cross-sectional view of part of a drug eluting balloon according to an embodiment of the present application.

In the FIGURE:
100—balloon body; 200—coating layer; 210—water-soluble adhesive layer; 220—isolating layer; 230—drug layer.

DETAILED DESCRIPTION

To make the objects, advantages and features of the present application more apparent, present application is described in detail by accompanying drawings in conjunction with the specific embodiments. It should be noted that the figures are provided in a very simplified form not necessarily presented to scale, with their only intention to facilitate convenience and clarity in explaining embodiments of present application. In addition, structures shown in the figures are usually portions of actual structures. In particular, as the figures tend to have distinct emphases, they are often drawn to different scales.

As used herein and in the appended claims, the singular forms "a", "an", and "the" include plural references unless the context clearly dictates otherwise. As used herein and in the appended claims, the term "or" is generally employed in its sense including "and/or" unless the content clearly dictates otherwise. The term "proximal" generally refers to the end that is close to a physician, and the term "distal" generally refers to the end that is close to a lesion sits of a patient. The term "inward" refers to a direction towards the axis of a balloon, and the term "outward" refers to a direction opposite to that described by "inward".

Environments in which drug eluting balloons and balloon catheters according to the present application can be applied include, but are not limited to: blood vessels that includes coronary arteries, peripheral arteries and cerebral arteries; and lumens that includes esophagus, airways, intestinal tract, biliary tract, cervix, urinary tract, prostate, joint cavities, intervertebral cavities, etc. Their particular applications include, but are not limited to, drug eluting balloons or balloon catheters for percutaneous coronary intervention treatments, peripheral vessel balloons or balloon catheters, intracranial vessel balloons or balloon catheters, urethral vessel balloons or balloon catheters, esophageal vessel balloons or balloon catheters, vertebral vessel balloons or balloon catheters, rotator cuff vessel balloons or balloon catheters, and so forth.

Referring to the sole FIGURE, a drug eluting balloon according to an embodiment of the present application includes a balloon body 100 and a coating layer 200. The coating layer 200 is provided on an outer surface of the balloon body 100 and includes a water-soluble adhesive layer 210, an isolating layer 220 and a drug layer 230, which are stacked (referring to laminate one on another) sequentially in this order from inside outward. The drug layer 230 is adhesive for adhering to and contacting with a lesion site (i.e., a target site). The water-soluble adhesive layer 210 is configured to dissolve under the flush action of blood flow after the dilation of the balloon body 100, so as to cause the detachment of the isolating layer 220 and the drug layer 230 from the balloon body 100. The isolating layer 220 is configured to reduce loss of the drug layer 230 taken away by the dissolution of the water-soluble adhesive layer 210 and to suppress the washing-away action of the blood flow on the drug layer 230 after the dissolution of the water-soluble adhesive layer 210.

After the drug eluting balloon is delivered to a lesion site, the balloon body 100 is dilated and the water-soluble adhesive layer 210 dissolves under the washing-away action of blood flow, so that the isolating layer 220 and the drug layer 230 detach from the outer surface of the balloon body 100 and adhere to the blood vessel wall. The arrangement of isolating layer 210 can effectively reduce loss of the drug layer 230 taken away by the dissolution of the water-soluble adhesive layer 210, and further suppress the washing-away action of blood flow on the drug layer 230 to reduce drug loss after the adherence and contact of drug layer 230 with the blood vessel wall. In this way, maximum intake of the drug by the blood vessel wall is able to be achieved, thereby improving utilization of the drug to reach an optimized therapeutic effect without increasing the dosage of the coated drug to avoid any toxic side effect incurred by overdosing. In addition, the isolating layer 220 allows significantly avoiding the flush action of blood flow on the drug layer while achieves sustained release of the drug layer 230 to get a prolonged period of therapeutic action, thereby optimizing the therapeutic effect.

Therefore, compared with existing drug eluting balloons, the drug eluting balloon provided in present application overcomes the problem of conflict between adhesion and detachment of the drug on the balloon and allows controlled detachment of the drug. In particular, during storage and transportation, the water-soluble adhesive layer provides adhesion to firmly secure the isolating layer and drug layer to the surface of the balloon body, so as to avoid the fall-off of isolating layer and drug layer. Once the drug eluting balloon is delivered to the targeted implant site, the balloon body is expanded, and the water-soluble adhesive layer dissolves under the flush action of blood flow, thus allowing detachment of the separation and drug layers. In one embodiment, the isolating layer 220 may be made of a degradable and film-forming water-resistant material that can be selected from a group consisting of cellulose-based material, polyester-based material, polyamino acid, chitin, chitosan-based material, silk fibroin, polyvinyl acetal (including polyvinyl formal and polyvinyl butyral). The cellulose-based material may include, but are not limited to, low-substituted nitrocellulose, cellulose acetate, silylated cellulose, acetylated cellulose, etc. The polyester-based material may include, but are not limited to, polylactic acid, polyglycolic acid, polylactic acid-glycolic acid copolymer, polycaprolactone, medical polyurethane, Polyhydroxyvalerate, poly-3-hydroxybutyrate or copolymers thereof, etc. The chitosan-based material may include, but are not limited to, chitosan or chitosan with additives, the additives including, but not limited to, polyether, gelatin, polysaccharides from *Chlorococcum* sp., pectin, apple polyphenol, etc.

Preferably, the isolating layer 220 may include a plasticizer selected from the group consisting of glycerol, castor oil, olive oil and combinations thereof. Preferably, the isolating layer 220 is present in the coating layer 200 at a weight percentage of 1%-20%, more preferably 5%-10%. Preferably, a weight ratio of the water-resistant degradable material to the plasticizer ranges from 1:1 to 1:2. The weight ratio of the water-resistant degradable material to the plasticizer may range from 1:1.2 to 1:1.5.

In one embodiment, the isolating layer 220 may be grafted at a bottom side thereof with molecules with antithrombotic ability, e.g., heparin, so as to provide an antithrombotic effect.

In one embodiment, the water-soluble adhesive layer 210 may be composed of a water-soluble macromolecular material and an excipient. Preferably, the water-soluble macromolecular may be composed of a starch-based natural macromolecular material, or a synthetic water-soluble macromolecular material, or a combination of these two. Preferably, the water-soluble adhesive layer 210 is present in the coating layer 200 at a weight percentage of 15%-50%, more preferably, 30%-40%. Preferably, the water-soluble macromolecular material is composed of a starch-based natural macromolecular and/or a synthetic water-soluble macromolecular material. The starch-based natural macromolecular material may be one or more selected from the group consisting of wheat starch, corn starch, tapioca starch, and modified forms thereof. The synthetic water-soluble macromolecular material may be one or more selected from the group consisting of polyacrylamide, hydrolyzed polyacrylamide, polyacrylic acid, carbomer, and calcium alginate. Preferably, a weight ratio of the starch-based natural macromolecular material to the synthetic water-soluble macromolecular material ranges from 1:1 to 5:1. The weight ratio of the starch-based natural macromolecular material to the synthetic water-soluble macromolecular material may range from 2:1 to 4:1. The water-soluble adhesive layer can both act, in a dry state, as a bonding agent for minimizing loss of the drug during transportation and delivery of the balloon, and gradually dissolve during delivery of the balloon to allow complete fall-off of the drug layer, thereby achieving the targeted controllable release of the drug.

In one embodiment, in order to increase/modify a dissolution speed of the water-soluble adhesive layer, the water-soluble adhesive layer 210 may be applied to the outer surface of the balloon body in a grid, stripe, spiral or other regular or irregular pattern.

In one embodiment, the drug layer 230 is composed of the drug selected from the group consisting of antiproliferative drug, anti-inflammatory drug, antiphlogistic drug, anti-hyperplasia drug, antibacterial drug, antineoplastic drug, anti-mitotic drug, cytostatic drug, cytotoxic drug, anti-osteoporotic drug, anti-angiogenic drug, anti-restenotic drug, microtubule-inhibitory drug, anti-metastatic drug and anti-thrombotic drug, together with a macromolecular excipient, so that the drug layer is able to firmly and tightly contact with the blood vessel wall and slowly release the drug to provide a prolonged therapeutic effect under protection of the isolating layer. Examples of the drug may include, but are not limited to, dexamethasone, prednisolone, corticosterone, budesonide, estrogen, sulfasalazine, aminosalicylic acid, aximethacin, aescinate, aminopterin, antimycoin, arsenic trioxide, aristolochic acid, aspirin, berberine, bilobol, rapamycin and its derivatives (including zotarolimus, everolimus, biolimus, 7-O-desmethyl rapamycin, temsirolimus, ridaforolimus, etc.), endostatin, angiostatin, angiopeptin, monoclonal antibodies capable of blocking the proliferation of smooth muscle cells, levofloxacin, paclitaxel, docetaxel, hydroxycamptothecin, vinblastine, vincristine, adriamycin, fluorouracil, cisplatin, thymidine kinase-inhibiting antibiotics (particularly actinomycin D), hormones, anti-cancer antibodies, bisphosphonates, selective estrogen receptor modulators, strontium ranelate, cyclosporin A, cyclosporin C and brefeldin A.

Preferably, the macromolecular excipient is selected from the group consisting of partially hydrolyzed polyvinyl alcohols (with a degree of hydrolysis of 87%-89%), polyvinylpyrrolidone and combinations thereof. Preferably, the drug layer 230 is present in the coating layer 200 at a weight percentage of 30%-80%, more preferably 40%-50%. A weight ratio of the drug to the macromolecular excipient may range from 1:1 to 1:5, more preferably from 1:2 to 1:3.

Further, embodiments of the present application also provide a method for manufacturing the drug eluting balloon, including the steps of:

(1) arranging the water-soluble adhesive layer onto the outer surface of the balloon body. The water-soluble adhesive layer may be coated on the balloon body directly and cover the entire circumference of the balloon body;

(2) arranging the isolating layer onto the water-soluble adhesive layer. The isolating layer may be coated on the water-soluble adhesive layer directly and the isolating layer is slightly shorter than the water-soluble adhesive layer in coating length. That is, two end portions of the water-soluble adhesive layer remains exposed. The exposed portions dissolves after contacting with the liquid, thereby facilitating detachment of the water-soluble adhesive layer from the balloon body; and (3) arranging the drug layer onto the isolating layer. Firstly, the macromolecular excipient is crosslinked by ultraviolet radiation. Then, the drug layer is formed by coating the drug onto the crosslinked macromolecular excipient. The drug layer also completely covers the isolating layer.

Besides, embodiments of the present application also provided a balloon catheter including the drug eluting balloon as discussed above. Those skilled in the art can properly configure other components of the balloon catheter according to prior art except for the drug eluting balloon, and a detailed description of how the balloon catheter is structured and works will be omitted for the sake of brevity. Since the balloon catheter provided in embodiments of the present application includes the drug eluting balloon as described above, it has the advantages brought by the drug eluting balloon, and reference can be made to the above embodiments for details in this regard.

Next, the preparation process of the drug eluting balloon according to present application is described in detail through several specific embodiments in conjunction with specific preparation methods, in order to further demonstrate features and advantages of the above embodiments.

Embodiment 1

This embodiment provides a preparation method of the drug eluting balloon, which include the following steps.

Step 1: Preparation and Application of the Water-Soluble Adhesive Layer.

5 g of a vegetable starch was dissolved in 100 mL of water with heating and stirring. Then, the starch solution is heated to 90° C. and maintains 30 minutes. The 1 wt. % aqueous solution of swollen polyvinyl alcohol (i.e., at a weight percentage of 1%) was added, resulting in a water-soluble glue solution. The balloon body 100 was immersed in the water-soluble adhesive solution for a period of time and then taken out, dried and cured. In this way, application of the water-soluble adhesive layer 210 to the balloon body 100 was achieved. The vegetable starch may be selected from the group consisting of wheat starch, corn starch, tapioca starch and combinations thereof. In this embodiment, the water-soluble macromolecular material was composed of only the starch-based natural macromolecular material and the polyvinyl alcohol act as the excipient.

Step 2: Preparation and Application of the Isolating Layer.

In a 60 mL mixed solution of ethanol and n-butyl acetate (v:v=1:2) (i.e., a volume ratio of ethanol and n-butyl acetate is 1:2), 6 g of nitrocellulose and 5 mL of glycerol were dissolved and stirred to form a homogeneous film-forming solution. The film-forming solution was then sprayed in a layer by ultrasonic spraying onto part of the surface of the water-soluble adhesive layer 210 (with two end portions of the water-soluble adhesive layer 210 remaining exposed) prepared in Step 1. Once the sprayed film-forming solution was dried and cured, the preparation and application of the isolating layer 220 were achieved.

Step 3: Preparation and Application of the Drug Layer.

In 100 mL of chloroform, 1.5 g of polyvinylpyrrolidone (PVP) was dissolved and stirred to form a homogeneous solution, which was then sprayed by ultrasonic spraying onto the surface of the isolating layer 220 prepared in Step 2 (without being sprayed out of the area of isolating layer 220). After being dried, the balloon was placed under an ultraviolet lamp and crosslink for 10 minutes to obtain a cross-linked PVP layer. A 6 mg/mL sirolimus solution in ethanol/water (v:v=8:2) was prepared, and 100 μL of the sirolimus solution was evenly applied onto the surface of the cross-linked PVP layer in a dropwise manner, followed by a drying process performed at 40° C. in vacuum. In this way, the preparation and application of the drug layer 230 were achieved.

The completion of Steps 1 to 3 resulted in the completion of the preparation and application of the whole coating layer 200, i.e. completion of the whole preparation process of the drug eluting balloon.

Embodiment 2

The preparation method of drug eluting balloon provide in this embodiment is substantially similar to that of embodiment 1. Only the differences between the two methods are described below.

Steps 1 and 2 in this embodiment are the same as those in embodiment 1, and this embodiment differ from embodiment 1 only in Step 3, i.e. preparation and application of the drug layer.

In 100 mL of chloroform, 1.5 g of polyvinylpyrrolidone (PVP) was dissolved and stirred to form a homogeneous solution, which was then sprayed by ultrasonic spraying onto the surface of the isolating layer 220 prepared in Step 2 (without being sprayed out of the area of isolating layer 220). After being dried, the balloon was placed under an ultraviolet lamp and crosslink for 10 minutes to obtain a cross-linked PVP layer. A 6 mg/mL zotarolimus solution in ethanol/water (v:v=8:2) was prepared, and 100 μL of the zotarolimus solution was evenly applied onto the surface of the cross-linked PVP layer in a dropwise manner, followed by a drying process performed at 40° C. in vacuum. In this way, the preparation and application of the drug layer 230 were achieved.

Embodiment 3

The preparation method of drug eluting balloon provide in this embodiment is substantially similar to that of embodiment 1. Only the differences between the two methods are described below.

Steps 1 and 2 in this embodiment are the same as those in embodiment 1, and this embodiment differ from embodiment 1 only in Step 3, i.e. preparation and application of the drug layer.

In 100 mL of chloroform, 1.5 g of polyvinylpyrrolidone (PVP) was dissolved and stirred to form a homogeneous solution, which was then sprayed by ultrasonic spraying onto the surface of the isolating layer 220 prepared in Step 2 (without being sprayed out of the area of isolating layer 220). After being dried, the balloon was placed under an ultraviolet lamp and crosslink for 10 minutes to obtain a cross-linked PVP layer. A 6 mg/mL paclitaxel solution in ethanol/water (v:v=8:2) was prepared, and 100 μL of the paclitaxel solution was evenly applied onto the surface of the cross-linked PVP layer in a dropwise manner, followed by a drying process performed at 40° C. in vacuum. In this way, the preparation and application of the drug layer 230 were achieved.

Embodiment 4

The preparation method of drug eluting balloon provide in this embodiment is substantially similar to that of embodiment 1. Only the differences between the two methods are described below.

Steps 1 and 3 in this embodiment are the same as those in embodiment 1, and this embodiment differ from embodiment 1 only in Step 2, i.e. preparation and application of the isolating layer.

In a 60 mL mixed solution of ethanol and n-butyl acetate (v:v=1:3), 1 g of chitosan, 5 g of polyvinyl alcohol, 0.5 g of carbomer and 8 mL of olive oil were dissolved and stirred to form a homogeneous film-forming solution. The film-forming solution was then sprayed in a layer by ultrasonic spraying onto part of the surface of the water-soluble adhesive layer 210 (with two end portions of the water-soluble adhesive layer 210 remaining exposed) prepared in Step 1. Once the sprayed film-forming solution was dried and cured, the preparation and application of the isolating layer 220 were achieved.

Embodiment 5

The preparation method of drug eluting balloon provide in this embodiment is substantially similar to that of embodiment 1. Only the differences between the two methods are described below.

Steps 1 and 3 in this embodiment are the same as those in embodiment 1, and this embodiment differ from embodiment 1 only in Step 2, i.e. preparation and application of the isolating layer.

1 g of chitosan, 5 g of medical polyurethane and 5 mL of castor oil were dissolved in a 60 mL of dimethylformamide (DMF) and stirred to form a homogeneous film-forming solution. The film-forming solution was then sprayed in a layer by ultrasonic spraying onto part of the surface of the water-soluble adhesive layer 210 (with two end portions of the water-soluble adhesive layer 210 remaining exposed) prepared in Step 1. Once the sprayed film-forming solution was dried and cured, the preparation and application of the isolating layer 220 were achieved.

Comparative Embodiment

A drug-coated balloon was prepared by applying a solution of sirolimus and iopromide (w/w=1:1) in acetone onto the surface of an ordinary balloon through the ultrasonic spraying and then drying the applied solution naturally.

Test on Loss During Delivery

Each of the drug-coated balloons prepared in Embodiments 1-5 and Comparative Embodiment was delivered in an in vitro blood vessel model, and the time to reach the targeted site was controlled to 60 seconds. The balloon was taken out from the model without implement of dilation. The residual amount of the drug onto the balloon surface was measured by high performance liquid chromatography (HPLC) and the drug loss during delivery was calculated.

Test on Absorption in Tissue

A segment of an isolated porcine artery keeping at a constant temperature of 37° C. was expanded by a sterilized bare balloon at 6 atm for 1 minute, followed by constriction and removal of the balloon. Next, each of the drug-coated balloon prepared in above embodiments was placed into the pre-expanded blood vessel for dilation at 6 atm for 1 minute, and the balloon was then constricted and removed from the blood vessel. After that, the blood vessel was immediately washed with phosphate-buffered saline (PBS). A concentration of the drug in the tissue and a residual amount of drug on the balloon surface were then measured by gas chromatography/mass spectrometry (GC-MS).

Test on Persistence Time in Tissue

Each of the drug-coated balloons prepared in the above embodiments was placed into a segment of an isolated porcine artery for dilation at 6 atm for 1 minute, and the balloon was then constricted and removed from the blood vessel. After that, the blood vessel was immediately washed with PBS and then incubated in a culture medium for 7 and 28 days. Samples were taken on Day 7 and 28, and concentrations of the drug in tissue were measured by GC-MS.

TABLE 1

Drug Loss During Delivery, Immediate Drug Concentration in Tissue and Drug Absorption in Tissue for Drug-Coated Balloons Prepared in Various Embodiments

|  | Drug Loss during Delivery | Concentration in Tissue (ng/mg) | Drug Absorption in Tissue (%) |
|---|---|---|---|
| Embodiment 1 | 3.2% | 424.8 ± 84.1 ng/mg | 51% |
| Embodiment 2 | 2.9% | 507.5 ± 121.6 ng/mg | 60% |
| Embodiment 3 | 3.1% | 481.7 ± 124.3 ng/mg | 45% |
| Embodiment 4 | 4% | 382.4 ± 98.5 ng/mg | 41% |
| Embodiment 5 | 3.7% | 412.4 ± 132.1 ng/mg | 54% |
| Comparative Embodiment | 27% | 184.4 ± 66.1 ng/mg | 15% |

TABLE 2

Drug Concentration in Tissue over Time for Drug-Coated Balloons Prepared in Various Embodiments

|  | Concentration in Tissue (ng/mg) | |
|---|---|---|
|  | Day 7 | Day 28 |
| Embodiment 1 | 358.2 ± 87.9 | 256.1 ± 85.7 |
| Embodiment 2 | 374.8 ± 102.2 | 232.4 ± 96.4 |
| Embodiment 3 | 402.1 ± 122.1 | 296.3 ± 136.1 |
| Embodiment 4 | 325.3 ± 110.3.1 | 198.5 ± 65.2 |
| Embodiment 5 | 345.1 ± 75.3.5 | 246.9 ± 103.6 |
| Comparative Embodiment | 15.1 ± 3.5 | BQL |

BQL - Below Limit of Detection

As can be seen from the experimental results, the drug eluting balloons prepared in the above embodiments each exhibit a drug loss rate during delivery lower than 4% and a tissue absorption rate greater than 41%, thereby enabling to achieve a low drug loss rate and a high tissue absorption rate. In addition, the arrangement of the isolating layer enables the sustained release of drug and hence achieves a prolonged therapeutic effect of the drug.

It should be noted that embodiments in present application are described in a progressive manner, with the description of each embodiment focusing on its differences from others. Reference can be made between the embodiments for their identical or similar parts. In addition, parts of different embodiments may be used in any combination, which is not limited in present application.

The description presented above is merely that of a few preferred embodiments of the present application and does not intend to limit the scope of present application in any sense. Any changes and modifications made by those of ordinary skill in the art based on the above disclosure fall within the protection scope as defined in the appended claims.

What is claimed is:

1. A drug eluting balloon, comprising a balloon body and a coating layer arranged on an outer surface of the balloon body, wherein the coating layer comprises a water-soluble adhesive layer, an isolating layer and a drug layer that arranged sequentially from inside outward, wherein the water-soluble adhesive layer covers all or partial of the outer surface of the balloon body, and the isolating layer incompletely covers the water-soluble adhesive layer, wherein at least one end portion of the water-soluble adhesive layer is not covered by the isolating layer.

2. The drug eluting balloon according to claim 1, wherein the isolating layer comprises a water-resistant degradable material selected from the group consisting of cellulose-based materials, polyester-based materials, chitosan-based materials, polyamino acid, chitins, polyvinyl acetals and combinations thereof.

3. The drug eluting balloon according to claim 2, wherein the isolating layer further comprises a plasticizer selected from the group consisting of glycerol, castor oil, olive oil and combinations thereof.

4. The drug eluting balloon according to claim 3, wherein a weight ratio of the water-resistant degradable material to the plasticizer ranges from 1:1 to 1:2.

5. The drug eluting balloon according to claim 1, wherein the isolating layer is present in the coating layer at a weight percentage ranging from 1% to 20%.

6. The drug eluting balloon according to claim 1, wherein the water-soluble adhesive layer covers the outer surface of the balloon body in a grid, stripe or spiral pattern.

7. The drug eluting balloon according to claim 1, wherein the water-soluble adhesive layer comprises a water-soluble macromolecular material selected from the group consisting of starch-based natural macromolecular materials, synthetic water-soluble macromolecular materials and combinations thereof.

8. The drug eluting balloon according to claim 7, wherein the water-soluble macromolecular material comprises a starch-based natural macromolecular material and a synthetic water-soluble macromolecular material, a weight ratio of starch-based natural macromolecular material to synthetic water-soluble macromolecular material ranging from 1:1 to 5:1.

9. The drug eluting balloon according to claim 1, wherein the water-soluble adhesive layer is present in the coating layer at a weight percentage ranging from 15% to 50%.

10. The drug eluting balloon according to claim 1, wherein the drug layer comprises a drug and a macromolecular excipient, and the macromolecular excipient is selected from the group consisting of partially hydrolyzed polyvinyl alcohols, polyvinylpyrrolidone and combinations thereof.

11. The drug eluting balloon according to claim 10, wherein the drug and the macromolecular excipient are present at a weight ratio ranging from 1:1 to 1:5.

12. The drug eluting balloon according to claim 1, wherein the drug layer is present in the coating layer at a weight percentage ranging from 30% to 80%.

13. A balloon catheter comprising the drug eluting balloon according to claim 1.

* * * * *